(12) United States Patent
Kabir et al.

(10) Patent No.: US 9,527,059 B2
(45) Date of Patent: Dec. 27, 2016

(54) FIELD SAMPLING KIT FOR CHEMICAL RECOVERY, STORAGE, AND PROFILING, METHOD OF MAKING AND USING THE KIT, AND DYNAMIC FABRIC PHASE SORPTIVE EXTRACTION (DFPSE) MEDIUM

(71) Applicant: THE FLORIDA INTERNATIONAL UNIVERSITY BOARD OF TRUSTEES, Miami, FL (US)

(72) Inventors: Abuzar Kabir, Dhaka (BD); Kenneth G. Furton, Homestead, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

(21) Appl. No.: 14/660,153

(22) Filed: Mar. 17, 2015

(65) Prior Publication Data
US 2015/0258542 A1    Sep. 17, 2015

Related U.S. Application Data

(60) Provisional application No. 61/954,293, filed on Mar. 17, 2014.

(51) Int. Cl.
*B01L 3/00* (2006.01)
*B01L 99/00* (2010.01)
(Continued)

(52) U.S. Cl.
CPC ........... *B01J 20/3212* (2013.01); *B01J 20/286* (2013.01); *B01J 20/321* (2013.01);
(Continued)

(58) Field of Classification Search
CPC .................................. B01J 20/00; B01L 99/00
(Continued)

(56) References Cited

U.S. PATENT DOCUMENTS 6,759,126 B1 *   7/2004   Malik ................ B01J 20/28014
                                                              428/375
6,825,046 B1 *  11/2004   Forsyth .................... G01N 1/12
                                                              422/527
(Continued)

*Primary Examiner* — Jill Warden
*Assistant Examiner* — Jacqueline Brazin
(74) *Attorney, Agent, or Firm* — Saliwanchik, Lloyd & Eisenschenk

(57) ABSTRACT

A field kit for collecting analytical samples has one or more dynamic fabric phase sorptive extraction (DFPSE) devices and/or fabric phase sorptive extraction (FPSE) devices and a plurality of containers for storing and transporting the DFPSEs and/or FPSEs that were used for sampling. The field kit has media for documenting information concerning the site, quantity, date, and/or other pertinent information concerning the sampling. Samples can be maintained within the kit for any required period of storage. Sampling can be done once or a plurality of times, such that an initial analysis can be carried out and analysis can be repeated using a portion of a FPSE or with a redundant FPSE that has been stored. The DFPSE device is a sampling device including a plurality of FPSEs, such that a number of different types of analytes can be sampled in different layers of the DFPSE. At least one external surface layer of the DFPSE is a barrier FPSE that restricts solids from underlying layers.

7 Claims, 7 Drawing Sheets

(51) Int. Cl.
*B01J 20/32* (2006.01)
*B01J 20/286* (2006.01)
*G01N 1/40* (2006.01)
*G01N 1/02* (2006.01)

(52) U.S. Cl.
CPC ......... *B01J 20/3204* (2013.01); *B01J 20/328* (2013.01); *B01J 20/3276* (2013.01); *B01J 20/3285* (2013.01); B01J 2220/64 (2013.01); G01N 1/405 (2013.01); G01N 2001/027 (2013.01)

(58) Field of Classification Search
USPC .......................................................... 422/430
See application file for complete search history.

(56) References Cited

U.S. PATENT DOCUMENTS

| | | | |
|---|---|---|---|
| 6,905,031 B1 * | 6/2005 | Miller | B01J 20/28019 210/470 |
| 6,929,778 B2 * | 8/2005 | Nunes | B01L 9/54 422/430 |
| 7,674,631 B2 * | 3/2010 | Pawliszyn | G01N 1/40 422/500 |
| 2006/0160064 A1 * | 7/2006 | Carbonell | B01D 15/00 435/4 |
| 2014/0274660 A1 | 9/2014 | Kabir et al. | |

* cited by examiner

FIELD SAMPLING KIT FOR CHEMICAL RECOVERY, STORAGE, AND PROFILING, METHOD OF MAKING AND USING THE KIT, AND DYNAMIC FABRIC PHASE SORPTIVE EXTRACTION (DFPSE) MEDIUM

CROSS-REFERENCE TO RELATED APPLICATION

This application claims the benefit of U.S. Provisional Application Ser. No. 61/954,293, filed Mar. 17, 2014, the disclosure of which is hereby incorporated by reference in its entirety, including all figures, tables and drawings.

BACKGROUND OF INVENTION

Solid Phase Extraction (SPE) is an exhaustive sample preparation technique where a sample is cleaned and the target analyte(s) are pre-concentrated using sorbent chemistry, primarily via a coating on the surface of silica particles that accomplishes the quantitative recovery of one or more target analytes that are contained in simple to extremely complex sample matrices. When the sample matrix is complex, containing particulates, proteins, lipids, debris, or other structures, one or more time consuming sample matrix clean-up steps, such as filtration, centrifugation, or protein precipitation, are often required, which can result in significant loss of analyte. Typically, small silica particles are used to support the coating of sorbent materials. The coated silica particles are packed in a sorbent bed having the geometric format of, for example, a disc, cartridge, or cylinder. The sorbent bed can exert enough resistance to flow of an aqueous solution containing the target analytes that the imposition of a pressure differential is required for the extraction process.

Surface-bonded hybrid organic-inorganic polymer coatings and monolithic beds are popular sorbents for use in analytical microextraction. These systems display high chemical stability and offer a diverse array of extracting phases for solvent-free/solvent-minimized analytical sample preparation. The availability of a wide variety of sol-gel precursors and sol-gel active organic polymers allows facile synthesis of advanced material systems with unique selectivity, enhanced extraction sensitivity and high thermal, mechanical and solvent stability. These sol-gel derived hybrid organic-inorganic advanced material systems have been shown to be effective in solvent-free/solvent-minimized sample preparation for a wide variety of analytes with biological, environmental, clinical, toxicological, food, pharmaceutical, bio-analytical, and forensic significance.

Sol-gel technology for the preparation of solid phase microextraction (SPME) sorbents has solved many limitations of conventional coatings. Sol-gel coatings are chemically bonded to many substrates, such as silica, when the gel is formed from the sol solution in the presence of the substrate. Because of the wide variety of possible sol components, sol-gel technology allows the synthesis of a large number of sorbents for SPME with large surface area, unique selectivity, and high thermal and solvent stability. Sol-gel monolithic beds are capable of achieving very high sample pre-concentration factors. The versatility of sol-gel technology allows the creation of surface-bonded sorbent coatings on unbreakable fiber materials (e.g., Ni—Ti, stainless steel, titanium, and copper) and also on substrates of different geometrical formats such as planar SPME (PSPME), and membrane SPME (MSPME). Sol-gel technology is adaptable to forming multi-component materials that have customized surface morphologies, selectivities and affinities of the sorbent. A wide variety of sol-gel silica, titania, zirconia, alumina, and germania-based precursors are commercially available. Additionally, a wide range of sol-gel reactive organic ligands are available to design hybrid organic-inorganic sol-gel coatings that can be used to target a particular analyte or sample matrix with improved selectivity, sensitivity, extraction phase stability and performance.

There remains a strong need for microextraction devices that permit the acquisition of very low concentrations of analytes that are present in a wide range of environments. Most microextraction devices are suited to a particular type of environment, and are often poorly suited for other environments. For example, some microextraction devices are well suited to sample air or other gases while others are suited for extraction from water or other liquids. Few microextraction devices can be easily adapted for sampling a solid surface. In addition, the limitation inherent to the geometric configurations of microextraction devices (smaller substrate surface area in both fiber and in-tube format) does not allow using a high amount of sorbent materials for extraction. The physical immobilization of polymeric materials on the substrate surface in microextraction devices limits their exposure to high temperature for thermal desorption and to organic solvents for solvent mediated desorption. As a result, many compounds with high boiling points and high polarity are still beyond the reach of microextraction devices. Microextraction devices are not recommended to make direct contacts with the sample matrix when it contains a high volume of particulates, debris or other matrix interferences that may cause irreversible damage to the sorbent coating.

A sampling device that can permit a uniform sampling of a broad variety of samples easily and effectively in the field is desirable, where more than one analyte, for example, neutral polar, nonpolar, organic acids, organic bases, heavy metals, and organometallics analytes, can be readily collected simultaneously during sampling, but where the collected analytes can be separately analyzed. There is a need for a sampling kit that comprises one or more easy-to-use devices that allow the acquisition of samples rapidly, reliably, and consistently when carried out by a skilled technician or even by an untrained individual that can follow the instructions with the kit, to allow for a high level of assurance that the samples are truly indicative of the analytes of interest.

DETAILED DISCLOSURE

Embodiments of the invention are directed to a field sampling kit that can be used for sampling trace and ultra-trace level of organic analytes and/or ionic analytes from sites that are of biological, chemical, environmental, toxicological, and forensic interest in locations remote from those with the instrumentation required for analysis of the analytes. The field sampling kit employs fabric phase sorptive extraction (FPSE) media which are sol-gel processed hybrid organic-inorganic polymeric networks anchored to one or more surfaces of a fabric comprising cellulose, polyester, carbon, silica or other natural or synthetic fibers as a composite flexible material. In an embodiment of the invention, the components of the kit are used in a method of field sampling where the extraction of trace or ultra-trace level of organic analytes and ionic analytes are of chemical, biological, pharmaceutical, forensic, toxicological, clinical, and/or environmental significance. The preparation of FPSEs is disclosed in A. Kabir and K. G. Furton, U.S. Provisional Application No. 61/787,910, entitled, Fabric Phase Sorptive Extraction (FPSE), and is incorporated herein by reference. Advantageously, samples can be used for immediate analysis while storing additional samples within the kit, preferably in a controlled environment, having proper chain of custody, as required. The stored samples are available for repeated or alternative analysis of the chemicals, if future judicial challenge of the chemical report is made, such that the analysis can be validated or augmented as required. By employing a field sample kit with the capacity to be the storage vessel of the field sample, it is possible to displace current methods and criteria for storage of biological, environmental, pharmaceutical, and toxicological samples that are neither uniform, convenient, nor inexpensive.

An embodiment of the invention is directed to Dynamic Fabric Phase Sorptive Extraction (DFPSE). DFPSE is an exhaustive sample preparation technique where a sample is cleaned and pre-concentrated using sorbent chemistry and substrate surface chemistry to accomplish high recovery of target analyte(s) contained in simple to extremely complex sample matrices without any sample matrix clean-up and achieve little or no analyte loss in a very short period of time. DFPSE uses a small device, such as a disc, cone or thimble, having a cellulose/polyester/nylon/glass microfibers/glass wool/carbon/composite with natural or synthetic flexible fabric as the substrate supporting and housing an organic polymeric material enclosed in its body having a sol-gel derived hybrid organic-inorganic polymeric sorbent coating on the surface and throughout the matrix attached via strong covalent bonding. The surface and matrix coatings are responsible for analyte extraction from different matrices.

Figure 1:
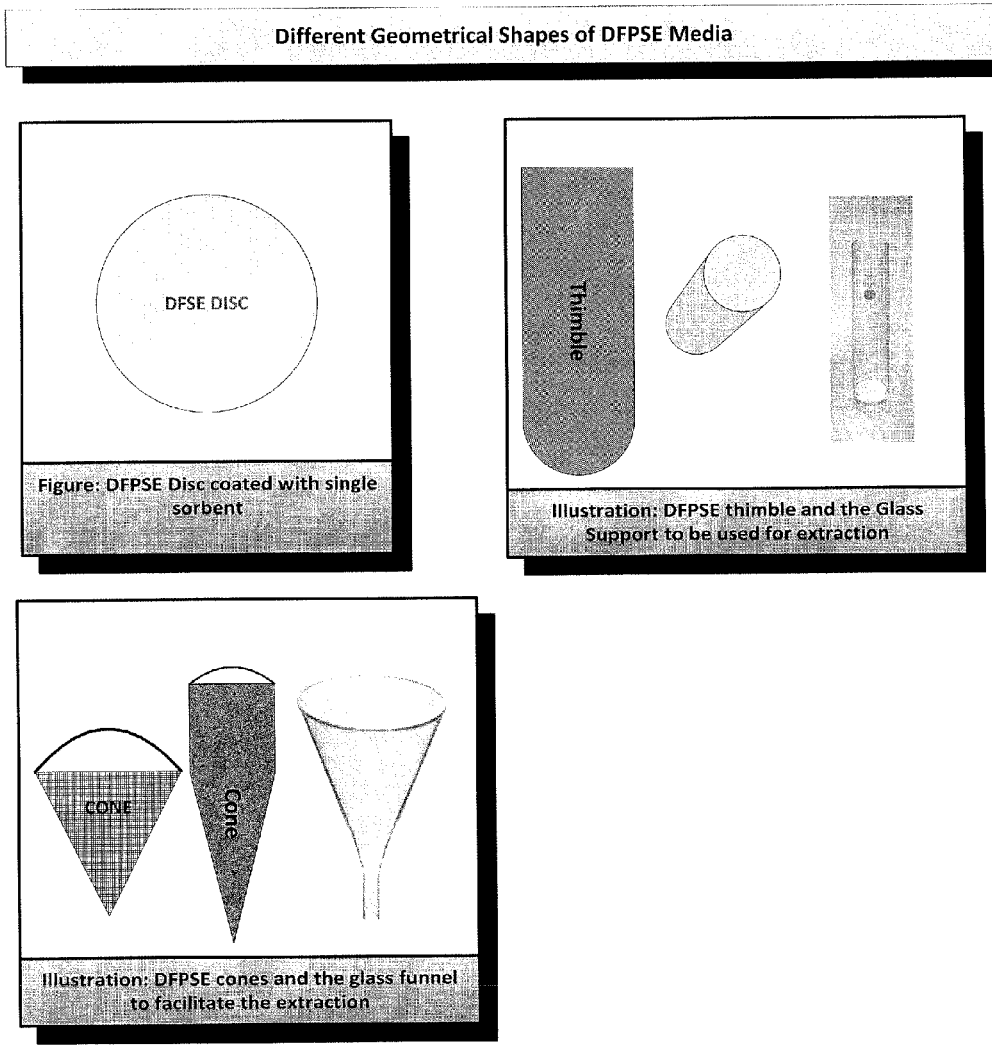
FIG. 1 shows different geometries of DFPSEs that can be employed, according to embodiments of the invention.
Figure 2:
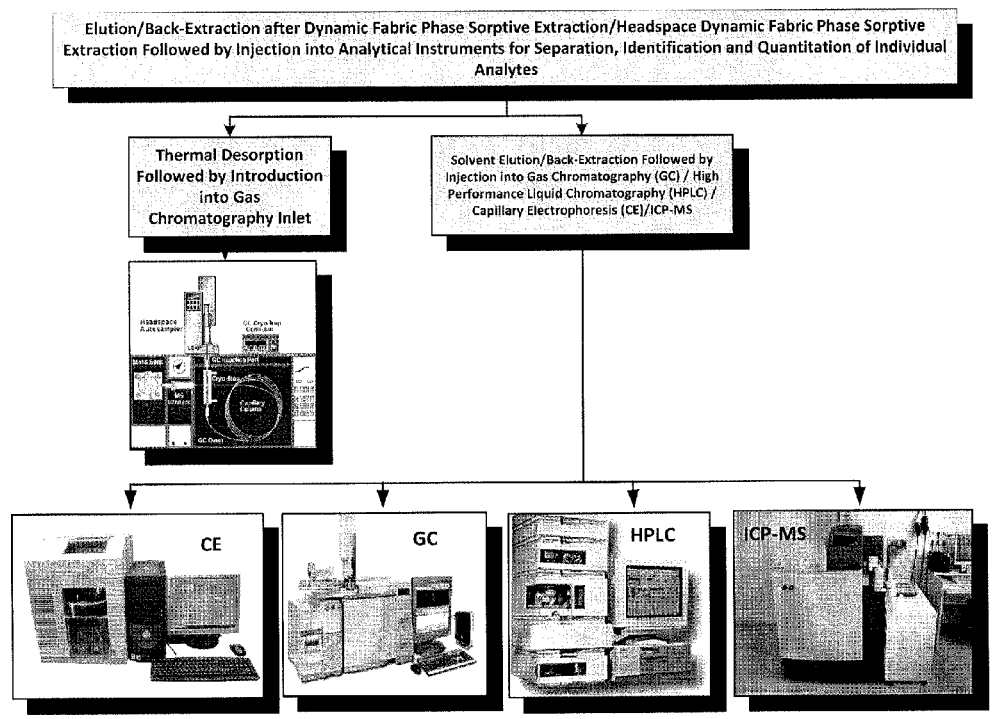
FIG. 2 shows analytical instrumentation that can be used for analysis of samples isolated using DFPSE media, according to embodiments of the invention.

DFPSE media can be in the form of circular disk, cone, thimble, and other suitable geometrical shapes, as illustrated in FIG. 1, compatible with various extraction devices. These media provide flexible, open, flat and easily accessible surfaces for sorbent-analyte interaction. Because both the surface and inner matrix of the substrate are coated with inherently porous sol-gel hybrid material, the accessible surface area for DFPSE media is not defined only by the exposed surface. The DFPSE media can be used in an equilibrium extraction mode as well as exhaustive extraction mode. The DFPSE can be employed in a flow-through system that extracts analytes exhaustively from the sample matrix. DFPSE requires only a small volume of organic solvent to back-extract or remove the extracted analytes from the DFPSE. Any organic solvent or solvent mixture can be used for the back-extraction as the composite coatings are chemically bonded to the surface of the fabric substrate. The solvent or mixture of solvents employed for back-extraction can be selected based on the analytical instrument, for example, a gas chromatography (GC) or a liquid chromatography (LC) that is used to detect and quantify the analytes. Examples of analytical systems that can be used with samples isolated by DFPSE media are shown in FIG. 2. The back-extraction can ensure no analyte carry-over when the DFPSE is recycled for subsequent extractions.

Figure 3:
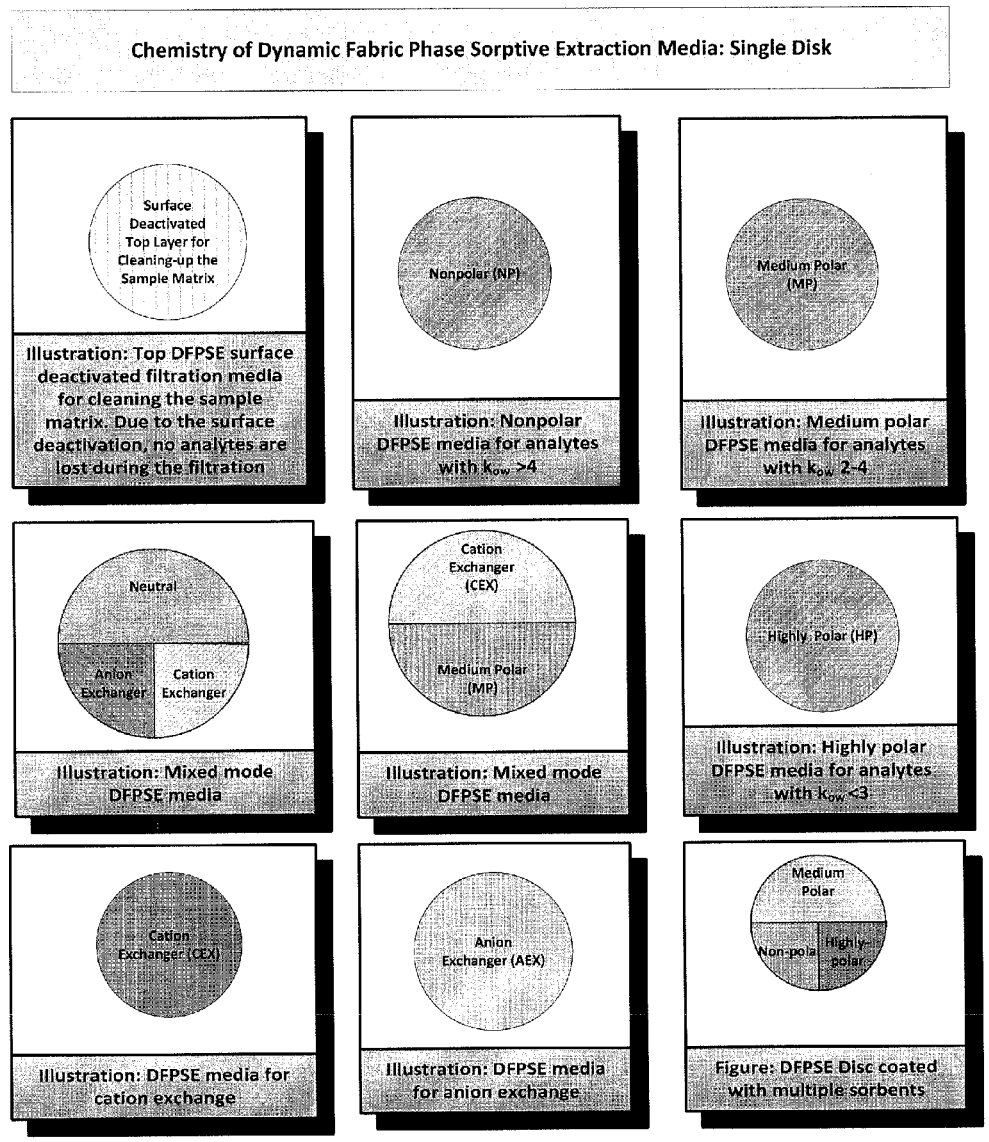
FIG. 3 shows different DFPSE disks where different types of analytes can be absorbed on different disks or a plurality of different analytes can be absorbed in different sections of a single disk, according to embodiments of the invention.
Figure 4:
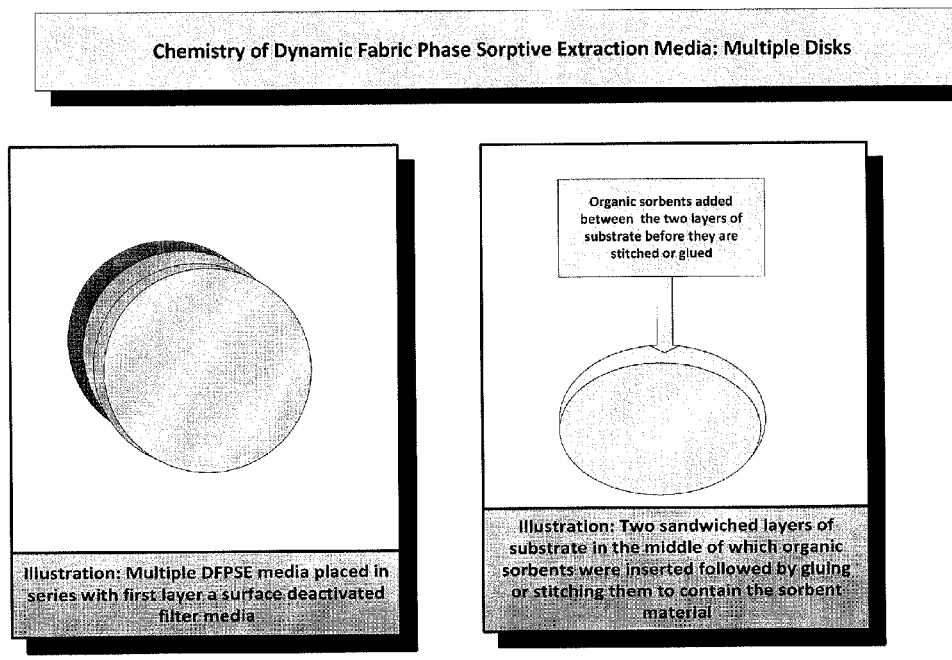
FIG. 4 shows DFPSE disks combinations where, left, different types of analytes can be absorbed on different stacked disks or, right, different analytes can be absorbed in different DFPSE disks or a sorbent material that is sandwiched between two disks, according to embodiments of the invention.

Hybrid organic-inorganic polymer coatings are generated on the surface of the fabric by sol-gel chemistry where strong covalent bonds are formed between the hybrid material and the fabric substrate. An almost endless number of coatings can be created with tunable selectivity, controlled porosity, and adjustable coating thickness by using selected inorganic precursor and organic polymers. The wide variety of DFPSE media that can be generated on, for example, a single disk can vary significantly with many different single types of coatings or a plurality of different types of coatings, as is illustrated in FIG. 3. The hybrid coating and the fabric substrate are chosen from those that demonstrate high chemical stability under a wide variety of conditions, such as exposure to high acidity and/or basicity, without compromising the integrity of the hybrid coating. In addition to use of multiple DFPSE disks for selective absorbing of different analytes, as shown in FIG. 4, left, two disks of the same or different coatings can be combined, adhered or stitched together, optionally with an absorbing material of the same or different affinity, and can be included in a compound disc, as shown in FIG. 4, right.

Figure 5:
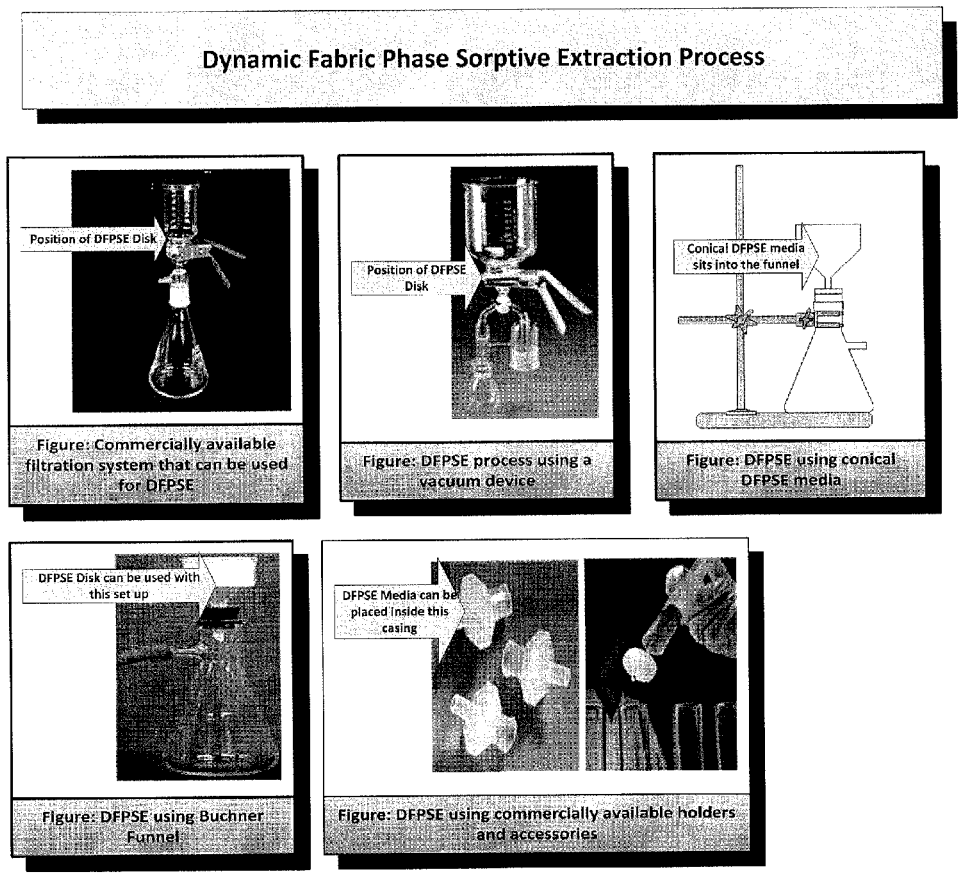
FIG. 5 shows filtration apparatus that can accept DFPSE media, according to embodiments of the invention.
Figure 6:
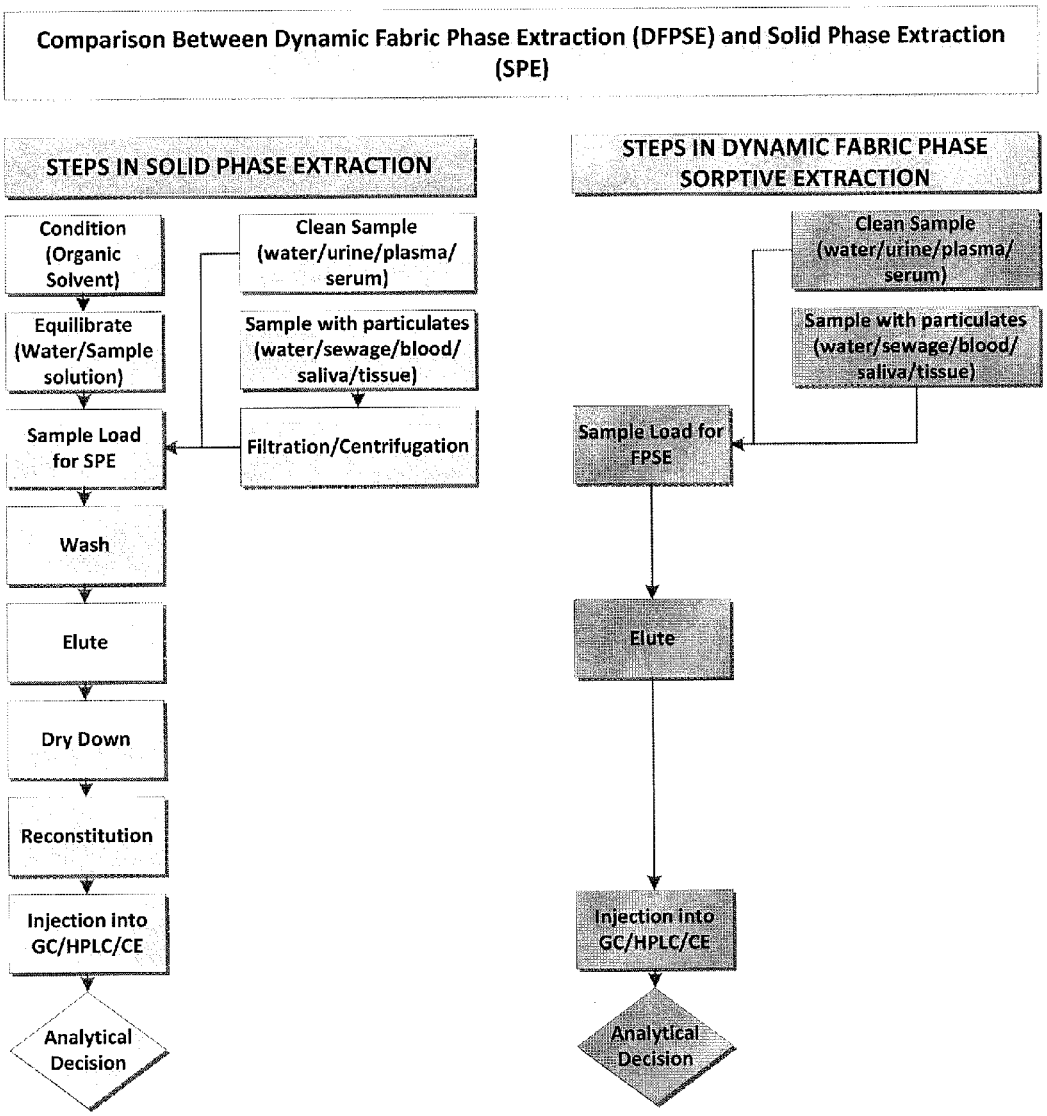
FIG. 6 outlines the method of analysis using DFPSE, right, according to embodiments of the invention, and prior art solid phase extraction (SPE), left.

Because the total surface area of the coated fabric is easily accessible for the analyte due to the DFPSE's open geometry, a complex sample matrix containing particles, debris, and other non-chemical interferences can be used without modification. Modification has the potential to result in analyte loss such that the extractant is not a true representation of the sample matrix. Having a high sorbent loading, the DFPSE medium demonstrates a high sample capacity. Extraction using DFPSE involves a relatively small number of operational steps and can be carried out in uncomplicated apparatus, as shown in FIG. 5, which does not require special operator training for use. The DFPSE media provide a relatively high volume of pre-concentrated extractant, allowing multiple injections into the analytical instrument, where the non-injected sample can be retained for subsequent analysis if the initially reported results are in dispute. DFPSE can be effectively used in field applications. DFPSE media can be used for extraction and back-extraction in situ without any specialized instrumentation that incurs additional costs and losses. The extractant can be transported in small HPLC/GC sample vials or other small containers to a remote analytical laboratory, where, for example, HPLC/GC sample vials can be sealed with septa that permits analysis without exposing the aliquot to the atmosphere. Due to the exceedingly high sorbent-analyte contact surface compared to SPME and SPE, DFPSE permits at least three orders of magnitude greater sensitivity than SPME. As indicated in the flow sheets shown in FIG. 6, the procurement and processing of analytical samples using DFPSE media requires fewer steps and minimizes losses and errors that are inherent to SPE and other multistep processes When the analytical scheme requires very high pre-concentration for ultra-trace analysis or other difficult sampling, multiple sheets of DFPSE media can be employed in independent extractions and combined for simultaneous back-extraction. For example, DFPSE allows the extraction of highly polar nitroaromatic explosives at parts per quadrillion (ppq) level concentrations, and such attributes of DFPSE is highly beneficial for analysis of emerging and persistent environmental pollutants.

DFPSE allows the use of fabric coated with polymers of different polarity. When the analytical scheme is to extract analytes having different polarities, multiple fabrics coated with different polarity can be employed. Subsequently, all extracted analytes can be back-extracted using a common back-extraction solvent.

A deactivated DFPSE medium can be used where a top layer is included to separate the sample matrix while retaining particulates and debris from dirty samples, and thereby protecting underlying DFSE media from unwanted materials. In this manner, DFPSE can be used multiple times without compromising extraction sensitivity. Consequently, the data quality can be significantly enhanced and the operational cost can be significantly reduced when DFPSE is used as the sample preparation technique.

Due to the flexibility of DFPSE media, one or more sol-gel coated DFPSE media of different coatings can be placed into cylindrical containment system for online extraction. A deactivated filtration system, having a sol-gel coated non-adsorptive fabric, can be used as a pre-DFPSE filter when a sample contains particulates, debris, fibers, protein, lipids, or other undesired components. The high permeability of deactivated filtration media does not generate any significant additional back pressure.

In an embodiment of the invention, a dynamic fabric phase sorptive extraction (DFPSE) medium is prepared that permits sample acquisition and preparation for a wide variety of samples by having various FPSE media combined as a plurality of FPSE layers. One or more surface layers of the DFPSE are inert FPSE media having no specific affinity towards organic compounds or ionic species, but are useful to filter particulates, debris, cells, tissues and other matrix interferents. One or more additional layers of the DFPSE media contain specific sorbent coatings that are selective towards neutral, acidic, basic, polar, apolar, cationic, or anionic analytes. The DFPSE allows for exhaustive extraction of the target analytes where the different types of analytes are partitioned to different layers of the DFPSE. Depending on the specific or general analytes suspected or targeted the number of layers to the DFPSE media can vary. The DFPSE media can store the FPSE bound extracted analytes in the various layers until the elution of the extract is to be performed for analysis in a gas chromatography, liquid chromatography, capillary electrophoresis, mass-spectroscopy, and/or other analytical instrument, generally at a remote laboratory to the site where the sample is acquired. The elution of the extracted analytes can be carried out with the individual FPSE layers separated from each other or while combined as the DFPSE. The DFPSE can conform to different shapes or be provided in different shapes that permit sampling of various gaseous, liquid, or solid environments. In an embodiment of the invention, the FPSE can conform to a surface and, as desired, be rolled or otherwise consolidated into a container that is used for the storage or removal of the analytes from the FPSE. The DFPSE can be planar squares, circles, or of any specialized shape matched to holders for sampling. The DFPSE can be in the form of a hemisphere, a cone, or other shape by where a specific volume of a liquid fluid can be placed and allowed to drain at a rate defined by the materials and geometry of the tillable DFPSE and any flow inducing means employed with the DFPSE.

The individual FPSEs comprise a fabric upon which a sol-gel coating is formed. Fabrics that can be used include natural fibers, such as, but not limited to, cotton, other cellulose fibers, silk, wool, and other keratin fibers, and synthetic fibers, such as, but not limited to, polyesters, glass fiber, polyamides, acrylics, polyethylene, polypropylene, polyvinylidene fluoride, polyacrylonitrile, cellulose acetate or any other synthetic polymer that can be spun/cast into fibers that can be combined into flexible fabrics. The fabric is generally a thin sheet that is knitted or woven or cast and cut or otherwise formed into sheets that are of a desired shape. The two-dimensional shape of the sheet may be defined by an implement for positioning the FPSE in a sampling environment, or to fit in a device for removing the absorbed analytes.

The sol-gel coating can be one that forms a flexible functional silicone or silicone copolymer rubber matrix on the fibers of the fabric. The sol-gel coating can be carried out by deposition of the sol on the fibers before spinning of the threads or yarns, before weaving or knitting of the fabric, or can be coated directly upon a woven or knitted fabric. Subsequent to coating, gelation can be carried out to form the sol-gel coating. The fibers coated with the sol can be gelled at any point before incorporation of the FPSEs into the DFPSE. The coating can be carried out by any deposition method including dip-coating, spray-coating, roll-coating, or any other method. The silicone or silicone copolymer can be deposited before functionalization, and the functionalization can be carried out after gelation where one or more base silicone or silicone copolymers can be functionalized subsequently, and the functionalization can occur in a base silicone or silicone copolymer that has one or more reactive functionalities that can be converted to a desired functionality, or functionalization can occur by a method by which an unfunctionalized silicone or the copolymer can be functionalized.

The silicone or silicone copolymer include specific functionality that selects a particular type of analyte, and can release the analyte under a specific set of conditions. For example, the FPSE can be a fabric with a silicone or silicone copolymer that has functionality that behaves as a cation exchange resin, where the fixed functionality is an anion with counter cations, for example, sodium ions, that can be displaced by the cations of interest in the analytical sample. The desired cationic analytes can be released by cationic exchange as the mode of removing the analyte for analysis. The FPSE can be functionalized as an anion exchange resin, where a functionality of the silicone or silicone copolymer is a fixed cation with an anion, such as chloride ion, that can be displaced by the anionic analyte and can be subsequently release as desired to form a free analyte for analysis. The FPSE can be functionalized as a bound acid, which can undergo an acid base reaction with a basic analyte to form a conjugate acid conjugate base pair that is bound to the FPSE until it is released for analysis by exposure to a stronger acid than that bound to the virgin FPSE or by exposure to a base that is a stronger base than the analyte. The FPSE can be functionalized as a bound base, which can undergo an acid base reaction with an acidic analyte to form a conjugate acid conjugate base pair that is bound to the FPSE until it is released for analysis by exposure to a stronger acid than the analyte or by exposure to a base that is a stronger base than that bound to the virgin FPSE. The FPSE can be functionalized by a bound small molecule or polymeric organic moiety that has an affinity for an organic species analyte preferentially to that of the fluid that contains the analyte. The FPSE bound moiety can be one that is selective for a polar or for a non-polar organic species. The analyte can be released from the organic species absorbing FPSE by exposing the FPSE to a solvent with a higher affinity to the bound organic moiety than the analyte or to a solvent that has a higher affinity for the analyte than does the bound organic moiety. The FPSE bound moieties can be a graphene-like molecule, for example, a polycyclic aromatic functionalized silicone or silicone copolymer that allows the bound aromatic moieties to undergo a pi-stacking type interaction with an aromatic analyte, but where the aromatic moiety can be released by contacting the analyte bound FPSE with a solution of one or more aromatic compounds that have a higher selectivity for the bound moieties or the aromatic analyte. Other moieties that can be modified for inclusion as bound functional groups in the sol-gel coating silicone or silicone copolymer include: polyvinyl alcohol (PVA); polyethyleneglycols; β-cyclodextrin; crown ethers; calixarenes; fullerenes; hydroxy-fullerenes; dendrimers; ionic liquids; sol-gel imprinted sites; bidentate ligands; polydentate ligands; or any other species that can be incorporated as selectively absorbing groups.

Figure 7:
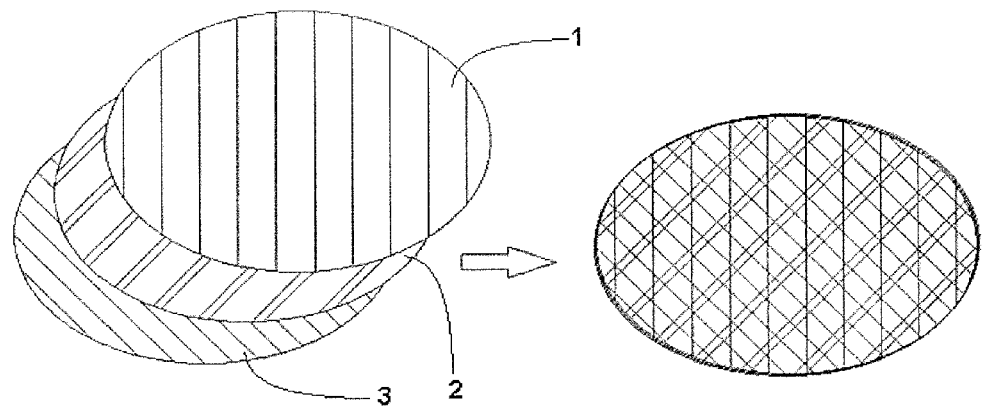
FIG. 7 shows the construction of a three-layer DFPSE having two different FPSEs for absorption of two different analytes and a barrier FPSE for removal of particulates, according to an embodiment of the invention.
Figure 8:
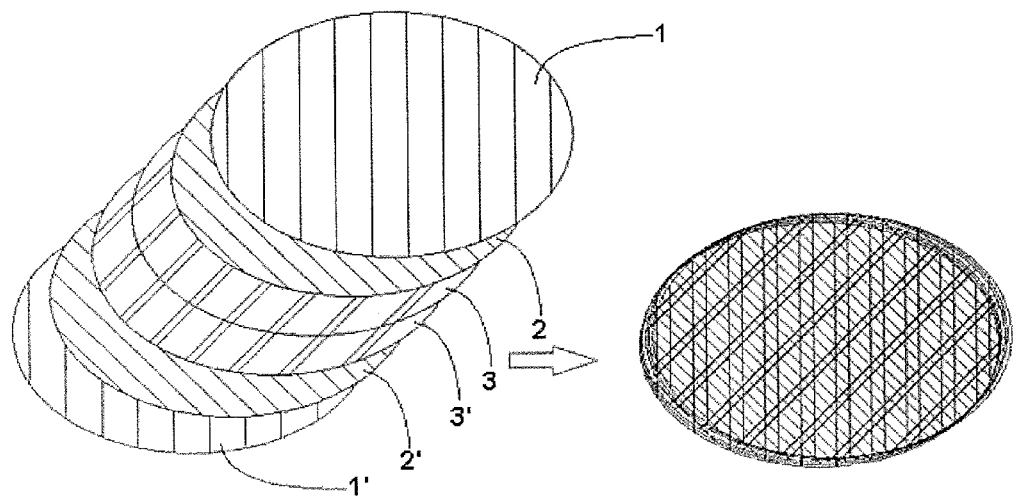
FIG. 8 shows the construction of a six-layer DFPSE having two different types of FPSEs with two layers of each type situated symmetrically between two barrier FPSEs, according to an embodiment of the invention.

In embodiments of the invention, a DFPSE is prepared by the preparation of a plurality of FPSEs that are fastened together to permit their use as a single sheet through which a fluid containing one or more suspected analytes is passed. A DFPSE containing a barrier FPSE 1 and two different functional FPSEs 2 and 3 is illustrated in FIG. 7. A surface FPSE, a barrier FPSE 1, can be one that is a silicone or silicone copolymer that is not functionalized for selectively absorbing any analyte and acts as a barrier to solids to allow the underlying functionalized FPSEs to be unencumbered by the solids during analyte loading, removal, and storage. Removal of the barrier FPSE can be carried out prior to analyte removal and/or storage. The individual FPSEs of a DSPE can be separated before or after storage, but, generally are separated before isolation of the bound analytes from the FPSE. Where the different FPSEs are selected, for example, to be compatible with a series of removing solvents, the DFPSE need not be disassembled into individual FPSEs prior to elution of the analytes for analysis. When one analyte is volatile and another in a separate FPSE layer is thermally stable at the temperature for volatilization, the elution of the two can be carried out without separation of the FPSE layers. A DFPSE can include one barrier FPSE and 1, 2, 3, 4, 5, 6, or more functionalized FPSEs. The DFPSE can have a barrier FPSE on both surfaces, top and bottom, such that either face can be employed as the barrier to solids. The DFPSE can have a plurality of like FPSEs 2 and 2' and 3 and 3' in addition to two barrier FPSEs 1 and 1', such that one of the like FPSEs 2 and 3 can be that used for an initial sample analysis and a second FPSE 2' and 3' can be stored for subsequent analysis, as is illustrated in FIG. 8. Having two barrier FPSEs allows the DSPE to be contacted from one face for a prescribed period of time or fluid volume and subsequently contacted from the opposite face for a like period of time or, if desired, for a different period of time than the prescribed period for the first face contacting. In this manner, two nearly identical samples for a given analyte can be taken using a single DSPE. In like manner, the DSPE can have two identical FPSEs for a second, third, fourth or n-th analyte, where, generally, but not necessarily, the arrangement of the FPSEs will have like FPSEs at equivalent proximities to the top and bottom barrier FPSEs.

The different FPSEs can be imprinted, color coded, or otherwise identified for the type of bound absorbent within that FPSE of the DFPSE, such that upon disassembly the appropriate FPSE is readily identified for use with the appropriate elution method and analytical method. The FPSEs of the DFPSE can be combined as a series of layers using mechanical fasteners, sewn threads, adhesives, or other means, where mechanical fasteners can be unbound, sewing threads can be easily removed, or adhesives can be readily removed by cutting a portion of the DFPSE, delaminating the FPSEs with the sheering of the adhesive, or by exposing the DFPSE to an agent that reacts with the adhesive and renders it non-adhesive.

A field sampling kit, according to an embodiment of the invention, is one that includes one or more DFPSEs, one or more FPSEs, or any combination thereof, and may additionally include other sampling solid phase extraction units, such that the kit allows transport to a sampling site, use of one or more of the DFPSEs, FPSEs, or other sampling units. The kit contains a redundancy of each type of analyte sample absorbent, such that two or more nearly identical samples can be taken. The kit also contains any or all of the following: a device or devices that can act as a holder of the DFPSEs or FPSEs to permit a fluid to flow through the holder and a DFPSE or FPSE or an ensemble of DFPSEs and/or FPSEs sequentially or simultaneously; instructions for use of each extraction unit; containers for storing the used extraction units, in a manner where they are clearly identified with respect to the site location, sampling time, and potential analytes or absorbent types; a means of disassembling a DFPSE into a plurality of FPSEs; and/or a means for recording any regulator records that must be maintained with the samples. A sampling kit can be customized to the type of analysis to be carried out. For example, a particular kit can be for use in analyzing for environmental pollution. Another kit can be one for forensic analysis of a crime scene. A sampling kit can be customized for analysis of pharmaceuticals, chemicals, drugs, explosives, nuclides, or poisons. A kit can be specialized for use with a gas sample, a liquid sample, or a wetted solid surface, or it can be a general kit that can be employed regardless of the nature of the analyte environment.

It should be understood that the examples and embodiments described herein are for illustrative purposes only and that various modifications or changes in light thereof will be suggested to persons skilled in the art and are to be included within the spirit and purview of this application.

We claim:
1. A dynamic fabric phase extraction (DFPSE) device, comprising: a plurality of stacked fabric phase extraction (FPSE) layers, wherein at least one of the FPSE layers is an analyte absorbing FPSE layer comprising at least one analyte absorbing FPSE medium; and at least one barrier FPSE layer on a top and/or bottom surface of the DFPSE, and wherein the analyte absorbing FPSE medium comprises a fabric substrate with a sol-gel coating that selectively absorbs a cationic analyte, anionic analyte, acidic analyte, basic analyte, polar organic analyte, or non-polar organic analyte.

2. The DFPSE device according to claim 1; wherein the analyte absorbing FPSE layers and the at least one barrier FPSE layers are combined mechanically, sewn, or adhered to each other.

3. The DFPSE device according to claim 1; wherein at least two of the analyte absorbing FPSE layers included for each target analyte to be extracted is disposed between two barrier FPSE layers, wherein the target analytes are selected from the cationic analytes, the anionic analytes, the acidic analytes, the basic analytes, the polar organic analytes, or the non-polar organic analytes, and wherein the FPSE layers of the same type are symmetrically disposed with respect to the center of the DFPSE and the two barrier FPSE layers.

4. A field kit for collection of one or more analytes, comprising:
   one or more dynamic fabric phase extraction (DFPSE) devices according to claim 1 and/or one or more fabric phase extraction (FPSE) devices;
   a plurality of containers for storing and transporting the DFPSEs and/or FPSEs that were used for sampling;
   documentation media, wherein information of the site, quantity, date, and other pertinent information concerning the sampling can be collected and maintained with the samples acquired using the kit.

5. The field kit according to claim 4, further comprising a holder for fixing one or more of the DFPSEs and/or one or more of the FPSEs during sampling.

6. The field kit according to claim 4, wherein the containers comprise an individual container for each analyte absorbing FPSE layer of the DFPSE.

7. The DFPSE device according to claim 1; wherein a plurality of different analyte absorbing FPSE layers target a plurality of different target analytes, and wherein the target analytes are selected from the cationic analytes, the anionic analytes, the acidic analytes, the basic analytes, the polar organic analytes, or the non-polar organic analytes.

* * * * *

UNITED STATES PATENT AND TRADEMARK OFFICE
CERTIFICATE OF CORRECTION

PATENT NO. : 9,527,059 B2  
APPLICATION NO. : 14/660153  
DATED : December 27, 2016  
INVENTOR(S) : Abuzar Kabir et al.

It is certified that error appears in the above-identified patent and that said Letters Patent is hereby corrected as shown below:

In the Specification

Column 6,  
Line 10, "the tillable" should read --the fillable--.

Signed and Sealed this  
Twentieth Day of June, 2017

Joseph Matal  
*Performing the Functions and Duties of the*  
*Under Secretary of Commerce for Intellectual Property and*  
*Director of the United States Patent and Trademark Office*